United States Patent [19]
Atlas

[11] Patent Number: 6,026,335
[45] Date of Patent: Feb. 15, 2000

[54] HEART RATE MONITOR WITH AGE-DEPENDENT TARGET-ZONE FEEDBACK

[76] Inventor: Dan Atlas, P.O. Box 271, Hod Hasharon 45102, Israel

[21] Appl. No.: 08/890,750

[22] Filed: Jul. 11, 1997

[30] Foreign Application Priority Data

Jul. 15, 1996 [IL] Israel ......................................... 118853

[51] Int. Cl.[7] ..................................................... G05B 9/02
[52] U.S. Cl. .............................. 700/83; 600/481; 600/520
[58] Field of Search ................................. 364/400, 410.1, 364/188, 189; 702/176, 178; 600/519, 520, 481; 704/270; 482/5, 8, 9, 901, 902

[56] References Cited

U.S. PATENT DOCUMENTS

| | | | |
|---|---|---|---|
| 4,420,000 | 12/1983 | Bailey ...................................... | 600/519 |
| 4,566,461 | 1/1986 | Lubell et al. ........................ | 600/520 X |
| 4,867,442 | 9/1989 | Matthews .................................... | 482/8 |
| 4,911,427 | 3/1990 | Matsumoto et al. ......................... | 482/9 |
| 5,301,154 | 4/1994 | Suga ..................................... | 600/520 X |
| 5,318,487 | 6/1994 | Golen et al. ................................ | 482/5 |
| 5,345,226 | 9/1994 | Rice, Jr. et al. .................... | 340/825.19 |
| 5,458,548 | 10/1995 | Crossing et al. ............................ | 482/6 |
| 5,577,510 | 11/1996 | Chittum et al. .......................... | 600/519 |
| 5,598,849 | 2/1997 | Browne .................................... | 600/520 |

*Primary Examiner*—William Grant
*Assistant Examiner*—Chad Rapp

[57] ABSTRACT

Improved methodology and apparatus for heart rate-related exercise through: (1) entering and storing and of user's age, as well as computing and storing of Maximal Heart Rate (MHR), (2) usage of programmable heart-rate target zone for benefit-specific training such as fat burning or strong heart, (3) computation of each target zone heart rate limits from the individualized age-related maximal heart rate, (e.g., specific fat-burning zone is 0.55 to 0.70 of the MHR for the specific user, and the strong heart zone is 0.7–0.85 of the MHR), (4) providing feedback of various exercise parameters (zone and time-in-zone, exercise elapsed time, etc.) through speech, (5) programming all the setup entry and feedback modes through a single push-button and "scrolling speech" menu, (6) utilization of two microcomputers to converse battery power, (7) integration of the entire apparatus into a chest belt, (8) automatic power-off upon removal of apparatus from the body, (9) programming new setup entry and feedback modes through a single push-button and "scrolling speech" menu via a preset combination of input pulses and input clicks.

14 Claims, 2 Drawing Sheets

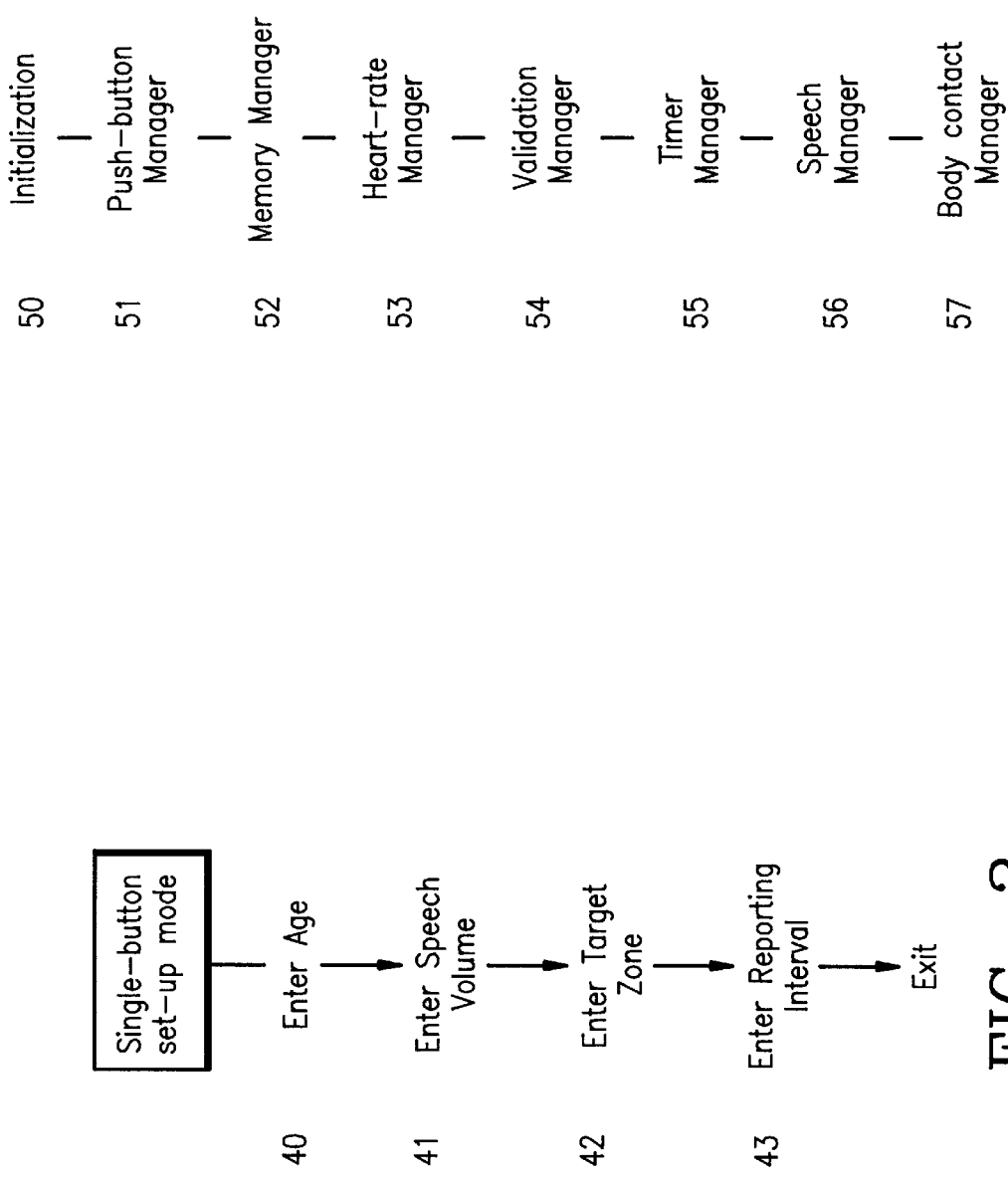

HEART RATE MONITOR WITH AGE-DEPENDENT TARGET-ZONE FEEDBACK

FIELD AND BACKGROUND OF THE INVENTION

This device and method belong to the class of exercise heart rate monitoring. The present invention relates generally to methodology and apparatus for heart rate monitoring in fitness and rehabilitation applications.

Such devices are applicable in facilitating the benefits from a structured exercise program during which the person has some knowledge or feedback from the heart rate. The target zones typically include fat burning, strong heart, aerobic, etc. The zones are individualized for each person, typically as heart rate limits based on age.

The present invention relates to a device and also to a method for employing a miniature talking device for monitoring of the heart work load during exercise. The device introduces manual means for entering user's age and desired exercise target zone for automated exercise.

The nature of devices and methods previously known and used are such as to require the user to memorize the heart rate limits suitable for a given exercise level. The mere feedback of heart rate requires the user of existing monitors to make some mental arithmetic: "Am I in the required zone which is between such and such to such and such beats per minutes?".

This invention is intended to be an improvement, attachment or replacement that overcomes the above difficulties and inconveniences which the existing monitors pose, especially to older people with slower thinking that are still engaged in exercise, or to the blind that can not use visual set-up and display devices altogether.

Traditional exercise heart rate monitors depend therefore on user's memory or on hi/lo limit alarms to maintain the pace for a desired target zone. The invention automatically presets all zones based on entered age, and user need not be concerned with the heart rate and target zone tables. User need only select the desired zone corresponding to the desired outcome: Fat burning, healthy heart, aerobics, etc.

Beyond the prior art of traditional display of the heart rate (speech or visual), the device provides the user with age-related feedback messages regarding presence and time-dwell in chosen training target zones, and prompting messages upon exceeding chosen zone limits.

The device automatically computes the individualized target zones as a percentage of the maximal heart rate (MHR). The MHR for approximately 70% of the population is typically 220-Age for men, and only slightly higher for women. The target zone for fat burning, for example, is in the zone corresponding to 55–70% of the individual MHR. Other zones include healthy heart, aerobic, anaerobic and red line zones.

The user needs only enter age and desired target zone. Feedback information is then automatically presented through digital display or preferred embodiment speech message in each chosen time period, or on-demand. The device combines speech messages and a single button for menu selection of age and zone setup.

The device stores such information in non-volatile memory. This device is of particularly great benefit to the blind exerciser or to people who exercise in poorly lit environments, as well as to those who wish to get the benefits of heart-rated exercise without resorting to heart-rate zone vs. age tables.

BRIEF SUMMARY OF THE INVENTION

The present invention relates to a device and also to a method for providing meaningful heart-rated feedback during exercise, including but not limited to weight reduction programs and rehabilitation training.

The invention is particularly useful to users that can not or do not want to memorize target zone formulas and rather have a monitoring device do it automatically upon entering individual's age and desired form of heart rate zone for effective exercise: aerobic, fat burning, anaerobic, and so on. It is particularly useful to the blind as the feedback is verbal.

The key advantage of the invention centers around the ability to individualize the monitoring function and feedback thereof to the user, primarily by entering into memory the user's age and desired type of exercise level.

The inventive idea which the new device and method embodies is individualization of the monitoring device to age, having a single button clicked like a PC mouse is all it takes to scroll through menus of age, zones and operational presets. In this way it overcomes the difficulties and inconveniences of previous devices and methods.

The way of using or putting the device into operation is simple. The user is prompted to scroll into the right age and zone by clicks on the bottom.

The device has peripheral pulse sensor/amplifier or ECG amplifier/filter for detecting the beat. The device has a microcomputer as means for measuring beat-beat intervals and an algorithm for computing the heart rate, while discarding extraneous pulses as artifacts. The device further contains a second microcomputer to allow both menu-driven set-up and information feedback via speech.

In summary, programming all the setup entry and feedback modes is provided through a single push-button and the "scrolling speech" menu. Two microcomputers are employed to conserve battery power, one being the low power master and the second being the high power speech generator and output earphones or speaker driver slave (the master controls the slave's sleep/awake cycles to disable the slave's power consumption during non-speech periods). The device is integrated into a chest belt comprising the electrodes. Alternatively it may be integrated into a head-band containing a pulse sensor and pulse amplifier and pulse detector instead of electrodes and ECG preamplifier with "R" wave detector. Furthermore, the heart rate may be derived from any other input including wireless or fiber-optic link. Various pre-programmed modes and features can be invoked by unique combinations of input pulses and push-button "enter" clocks. Finally, automatic power-off upon removal of apparatus from the body is provided for by software only, without sensing a physical resistance, capacitance or impedance between the electrodes. The later prevents movement artifacts due to test currents forced through the body, producing voltage changes across the changing body contact.

BRIEF DESCRIPTION OF THE DRAWINGS

FIG. 2 depicts the single button set-up sequence.

FIG. 3 depicts the key building blocks of the operating software other than set-up.

DESCRIPTION OF PREFERRED EMBODIMENT

Figure 1:
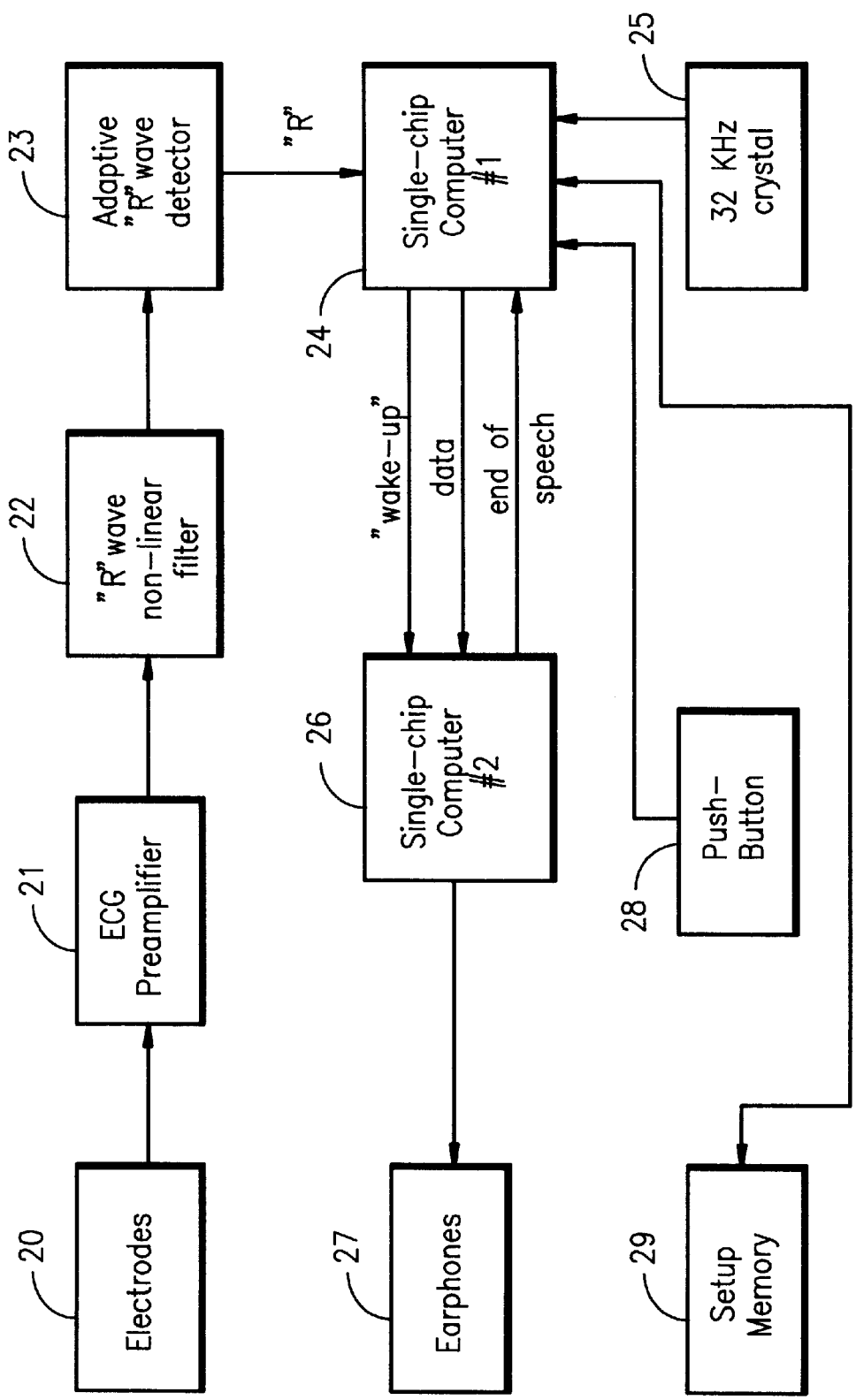
FIG. 1 depicts the preferred embodiment of the device as a block diagram of the hardware components.

With reference to FIG. 1, there is illustrated on form of a device and a method of implementing the invention. A set of electrodes 20 make contact with the chest, arms or arm-to-leg so as to pick up the heart's ECG signal. The signal is amplified and filtered by preamplifier 21, and the "R" wave portion of the signal is further filtered by a non-linear filter 22 and detected as a digital signal by an adaptive "R" wave detector 23.

The digital representation of the "R" wave is presented as an input to a single-chip computer #1 24. The #1 computer is a low power master device operating with approximately 32 kHz crystal 25. This #1 computer computes the heart rate, scans the push-button 28 and controls the operation of a slave computer #2 26 that stores and generates the speech messages as well as directly drives the earphones or speaker 27. The later is a high-current drain device operating at 7–11 MHz, and is put to sleep when speech message is not requested automatically or by manual demand through the push-button. Non-volatile memory 29 "remembers" the age, defaults and set-ups beyond power off and battery changes.

With reference to FIG. 2, there is illustrated the preferred embodiment sequence for using the push button in the setup mode. Using speech feedback, the device allows the user to click-in age 40, enter speech volume 41, the desired target zone for the exercise 42, and finally the reporting interval for automatic presentation 43 of speech messages of elapsed time, time-in-zone, etc. Once the set-up mode is completed, the software exits to the operating mode.

With reference to FIG. 3, there is illustrated the diagram of the key software modules that control the operation of the device. Upon first click of the push button the unit turns on and performs reset and initialization 50.

Thereupon the push-button manager 51 is scanned for further requests for re-entry to set-up mode (a long press) or a single or double presses to request on-demand information regarding present zone status, etc. Any set-up modification is stored by the non-volatile memory using the memory manager 52.

The device computes the heart rate and cleans up artifacts through the heart rate manager 53. The validity of the heart rate at any period is monitored by the validation manager 54. The elapsed time and time-in-zone computations are provided for by the timer manager 55.

The speech manager 56 controls computer #2 sleep and wake-up functions to converse battery power during non-speech periods.

Finally, the body contact manager 57 monitors the validation manager to obtain an indication that the device has been removed from the body. In such even the device will automatically turn off.

Although the invention has been described in detail for the purpose of illustration, it is to be understood and appreciated that such detail is solely and purely for the purpose of example, and that other variations, modifications and applications of the invention can be made by those skilled in the art without departing from the spirit and scope of the invention.

What is claimed is:

1. An exercise training device comprising a storage device having a single pushbutton for inputting selected data into said storage device;
    means within said storage device for providing setup value queries to a user, said setup values including the age of the user and the desired exercise program,
    wherein the user enters the user's age and desired exercise program into said storage device;
    means for detecting the heart rate of a user, said detecting means attached to said storage device and means for attaching said storage device to a user whereby the user's heart rate may be detected during exercise;
    wherein said storage device compares the user's heart rate with a target zone heart rate calculated by said storage device based on the age and exercise program inputted; and
    a device for providing feedback regarding the user's heart rate to the user during the exercise program.

2. An exercise training device as described in claim 1 wherein said device for providing feedback presents the feedback in an audio message.

3. An exercise training device as described in claim 2 wherein said audio message is a speech message.

4. An exercise training device as described in claim 1 wherein said feedback includes information regarding the user's heart rate as compared to the target zone heart rate.

5. An exercise training device as described in claim 1 wherein the target zone heart rate is 0.55 to 0.85 of the user's maximal heart rate, the maximal heart rate being equal to 220 minus the user's age.

6. An exercise training device as described in claim 5 wherein the target zone heart rate is 0.55 to 0.70 of the user's maximal heart rate.

7. An exercise training device as described in claim 5 wherein the target zone heart rate is 0.70 to 0.85 of the user's maximal heart rate.

8. An exercise training device as described in claim 1 wherein the device is attached to the chest of the user to detect the heart rate.

9. An exercise training device as described in claim 1 wherein the device is integrated into a headband to detect the heart rate.

10. An exercise training device as described in claim 1 wherein said means for providing setup value queries to a user comprises speech menu means for providing scrolling speech menu driven choices to the user.

11. An exercise training device as described in claim 1 wherein
    said means for providing setup value queries to a user comprises speech menu means for providing scrolling speech menu driven choices to the user.

12. An exercise training device comprising:
    a storage device having a single pushbutton for inputting selected menu-driven data into said storage device,
    speech menu means within said storage device for providing a scrolling speech menu driven choice of setup values queries to a user, said setup values including the age of the user and the desired exercise program requested; wherein the user
        enters the user's age into said storage device through said single pushbutton in response to a speech menu; and
        enters a specified exercise program desired into said storage device through said single pushbutton in response to a speech menu;
    means for attaching said storage device to a user whereby the user's heart rate may be detected during exercise;
    means for detecting the heart rate of a user, said detecting means attached to said storage device and comparing the heart rate with a target zone heart rate calculated by said storage device based on the age and exercise program inputted; and
    said speech device providing audible information to the user when the target heart rate zone has been entered.

13. An exercise training device as recited in claim 12 wherein said device is attached to the chest to detect the heart rate.

14. An exercise training device as recited in claim 12 wherein said device is integrated into a head band to detect the pulse rate.

* * * * *